(12) United States Patent
Solomon et al.

(10) Patent No.: US 11,109,846 B2
(45) Date of Patent: Sep. 7, 2021

(54) SYSTEM AND METHOD FOR PROVIDING ASSESSMENT OF TUMOR AND OTHER BIOLOGICAL COMPONENTS CONTAINED IN TISSUE BIOPSY SAMPLES

(71) Applicant: MEMORIAL SLOAN KETTERING CANCER CENTER, New York, NY (US)

(72) Inventors: Stephen B. Solomon, New York, NY (US); Jeremy C. Durack, New York, NY (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 73 days.

(21) Appl. No.: 15/118,037

(22) PCT Filed: Feb. 13, 2015

(86) PCT No.: PCT/US2015/015844
§ 371 (c)(1),
(2) Date: Aug. 10, 2016

(87) PCT Pub. No.: WO2015/123536
PCT Pub. Date: Aug. 20, 2015

(65) Prior Publication Data
US 2016/0367228 A1    Dec. 22, 2016

Related U.S. Application Data

(60) Provisional application No. 61/940,330, filed on Feb. 14, 2014.

(51) Int. Cl.
*A61B 10/02* (2006.01)
*A61B 6/00* (2006.01)
(Continued)

(52) U.S. Cl.
CPC ........ *A61B 10/0275* (2013.01); *A61B 5/0066* (2013.01); *A61B 5/0071* (2013.01);
(Continued)

(58) Field of Classification Search
None
See application file for complete search history.

(56) References Cited

U.S. PATENT DOCUMENTS

| | | | |
|---|---|---|---|
| 6,767,711 B2 * | 7/2004 | Bander | G01N 33/57434 435/7.1 |
| 8,137,642 B2 | 3/2012 | Hutchins et al. | |

(Continued)

OTHER PUBLICATIONS

International Search Report for International Patent Application No. PCT/US2015/015844 dated Jul. 8, 2015.
International Written Opinion for International Patent Application No. PCT/US2015/015844 dated Jul. 8, 2015.

*Primary Examiner* — Patrick Fernandes
*Assistant Examiner* — Benjamin S Melhus
(74) *Attorney, Agent, or Firm* — Hunton Andrews Kurth LLP

(57) ABSTRACT

An exemplary system, method and computer-accessible medium can include, for example, receiving information related to a scan(s) of a three-dimensional structure(s) containing a first tissue(s) and a second tissue(s), and providing the information to a system for identifying respective tissue types of the first tissue(s) and the second tissue(s). The structure(s) can be scanned to generate the information. The structure(s) can include a paraffin block(s). The first tissue(s) or the second tissue(s) can be excised. The tissue types can include a cancerous tissue and a non-cancerous tissue, and the first tissue(s) can be identified as the cancerous tissue and the second tissue(s) can be identified as the non-cancerous tissue.

20 Claims, 6 Drawing Sheets

(51) Int. Cl.
    *A61B 5/00*          (2006.01)
    *G01N 21/64*       (2006.01)
    *G01N 21/27*       (2006.01)
    *G01N 24/08*       (2006.01)
    *G01N 33/483*     (2006.01)
    *G01N 21/17*       (2006.01)

(52) U.S. Cl.
    CPC .............. *A61B 5/0075* (2013.01); *A61B 6/00* (2013.01); *G01N 21/17* (2013.01); *G01N 21/27* (2013.01); *G01N 21/6428* (2013.01); *G01N 24/08* (2013.01); *G01N 33/4833* (2013.01)

(56) References Cited

U.S. PATENT DOCUMENTS

| | | |
|---|---|---|
| 8,213,005 B2 | 7/2012 | Masilamani et al. |
| 2004/0121456 A1* | 6/2004 | Fischer .................. B01L 3/502 435/297.2 |
| 2006/0036173 A1 | 2/2006 | Kelly et al. |
| 2007/0167697 A1 | 7/2007 | Avila et al. |
| 2009/0092993 A1* | 4/2009 | Kallioniemi ......... C12Q 1/6809 435/6.14 |
| 2010/0032575 A1 | 2/2010 | Iagaru et al. |
| 2012/0328178 A1* | 12/2012 | Remiszewski ....... A61B 5/0071 382/133 |
| 2013/0183710 A1* | 7/2013 | Reifenberger ........... C12Q 1/68 435/29 |

\* cited by examiner

SYSTEM AND METHOD FOR PROVIDING ASSESSMENT OF TUMOR AND OTHER BIOLOGICAL COMPONENTS CONTAINED IN TISSUE BIOPSY SAMPLES

CROSS-REFERENCE TO RELATED APPLICATION(S)

The present application relates to and claims the benefit and priority from International Patent Application No. PCT/US2015/015844 filed Feb. 13, 2015 and published on Aug. 20, 2015 as International Publication No. WO 2015/123536, which claims the benefit and priority from U.S. Patent Application No. 61/940,330 filed on Feb. 14, 2014, the entire disclosures of which are incorporated herein.

FIELD OF THE DISCLOSURE

The present disclosure relates generally to biopsies, and more specifically, to exemplary embodiments of instrument, system and method for a rapid assessment of the presence of cancer tissue and/or Deoxyribonucleic acid ("DNA") presence and quantity of a tumor, as well as the presence and quantity of biological components relevant to medical diagnostics or biomedical research (e.g., genetic material, proteins, and metabolites) in tissue biopsy samples.

BACKGROUND INFORMATION

For cancer patients undergoing a needle biopsy, a primary concern can be biopsy safety, as well as obtaining a diagnosis that can enable a rapid and effective treatment, if treatment can be necessary. Unfortunately, the standard approach to on-site biopsy screening can fail to identify sample deficiencies in a significant number of patients, particularly when genetic testing can be essential. Personalized cancer therapies based on tumor characterization at the molecular level can be a goal of modern oncology. Currently, tumor profiles obtained from genomic analysis can enable precisely targeted treatments. While targeted therapies have improved, less progress has been made to optimize the process of the tissue acquisition (e.g., the tissue biopsy).

Preliminary studies examining results after image-guided percutaneous needle biopsies revealed that conventional methods can be insufficient to ensure the success of the intended molecular diagnostic tests. A conventional method to ascertain tissue sample adequacy at the time of needle biopsy examines the presence or absence of cytopathology on tissue preparations viewed by light microscopy (e.g., "imprint cytology"). The typical time used for slide review per sample can be approximately 3-5 minutes. Based on the cytotechnologist's interpretation of cell numbers, morphology, architecture and staining characteristics, repeated needle passes can be recommended. This feedback mechanism can increase the likelihood that samples will be sufficient and appropriate for diagnostic purposes. The imprint cytology approach needs the resources and experience needed to conduct rapid biopsy screening. However, this practice may not be ubiquitously utilized due to resource burden and cost, and additionally, can negatively impact the biopsy sample prior to histopathologic analysis. It is known that touch-preparations of core needle biopsy samples on glass slides can (i) misrepresent the quantity of neoplastic cells in the specimen by depleting the core sample of cancer cells, and (ii) disrupt tissue architecture and fragment core samples destined for diagnostic and molecular analysis.

The cost of biopsy failures can be measured in various ways. For hospitals, institutional resources, including disposable and fixed equipment and medical professional time, can be utilized without providing a clinically effective service. However, cancer patients themselves suffer the most critical costs of needle biopsy failures. As biopsy results frequently determine cancer treatment alternatives, a biopsy failure can result in delay of appropriate care. Achieving better outcomes in the era of personalized medicine can benefit from appropriate care, such as targeted anti-cancer drug therapies, as well as timely care. In addition to care delays, patients can be subject to increased risks from repeated biopsy attempts related to multiple needle insertions (e.g., bleeding, infection, or seeding of cancer cells along the needle path), as well as from sedation or anesthesia. In order to develop personalized treatment plans, the tissues used for research and clinical care can be commonly obtained via targeted, image-guided, core needle biopsies. Unfortunately, deficiencies in the current standard practice for on-site assessment of biopsy adequacy can often lead to failure of subsequent specimen analysis. These deficiencies can be particularly apparent during attempts to acquire the tissue from metastatic disease in bone, as existing techniques and assays may only be optimized for soft tissues.

Thus, it may be beneficial to provide exemplary systems, methods and computer-accessible mediums that can facilitate rapid cancer biopsy specimen screening, and which can overcome at least some of the deficiencies described herein above.

SUMMARY OF EXEMPLARY EMBODIMENTS

An exemplary system, method and computer-accessible medium can include, for example, receiving information related to a scan(s) of a three-dimensional structure(s) containing a first tissue(s) and a second tissue(s), and providing the information to a system for identifying respective tissue types of the first tissue(s) and the second tissue(s). The structure(s) can be scanned to generate the information. The structure(s) can include a paraffin block(s). The first tissue(s) or the second tissue(s) can be excised. The tissue types can include a cancerous tissue and a non-cancerous tissue, and the first tissue(s) can be identified as the cancerous tissue and the second tissue(s) can be identified as the non-cancerous tissue. Further information from the system can be received which can include an identification of the tissue type of the first tissue(s) and the second tissue(s). The scan(s) can be a three-dimensional scan of the three-dimensional structure(s), which can be performed using a computed tomography arrangement.

A further exemplary embodiment of the present disclosure can be a method for excising a first tissue(s) or a second tissue(s), which can include, for example, embedding the first tissue(s) and the second tissue(s) in a three-dimensional structure(s), scanning the three-dimensional structure(s), providing first results of the scan to a system for identifying respective tissue types of the first tissue(s) and the second tissue(s), receiving second results from the system including an identification of the tissue types of the first tissue(s) and the second tissue(s), and excising the first tissue(s) or the second tissue(s) based on the second results. The scan(s) can be a three-dimensional scan of the three-dimensional structure(s), which can be performed using a computed tomography arrangement.

In another exemplary embodiment of the present disclosure is an exemplary system, method and computer-accessible medium, which can include, for example, receiving information related to a scan(s) of labeled(s) tissue contained in a biopsy device, providing the information to a system for quantifying an amount of a biological component(s) contained within the labeled tissue(s). Information from the system can be received, which can include the amount of the biological component(s) contained within the labeled tissue(s). The biopsy device can include a biopsy needle. The labeled tissue(s) can include (i) a dye(s), (ii) a stain(s), (iii) a fluorescent label(s), (iv) a radioactive agent(s), or (v) a nuclear magnetic resonance tag(s). The biological component(s) can include (i) Deoxyribonucleic acid, (ii) Ribonucleic acid, (iii) a protein(s) and/or (iv) a metabolite(s).

Another exemplary embodiment of the present disclosure can be a method, which can include, for example, inserting a biopsy device(s) into a patient to remove a tissue sample(s), labeling the tissue sample(s), scanning the one labeled tissue sample(s) to obtain information regarding the labeled sample(s), and providing the information to a system for quantifying an amount of a biological component(s) contained within the labeled tissue(s). In some exemplary embodiments of the present disclosure, further information from the system can be received, which can include the amount of biological component(s) contained within the labeled tissue(s). The biopsy device can include a biopsy needle. The tissue sample can be labeled using (i) a dye(s), (ii) a stain(s), (iii) a fluorescent label(s), (iv) a radioactive agent(s), or (v) a nuclear magnetic resonance tag(s). The biological component(s) can include (i) Deoxyribonucleic acid, (ii) Ribonucleic acid, (iii) a protein(s) or (iv) a metabolite(s).

In some exemplary embodiments of the present disclosure, the structure(s) can include a paraffin, or other form of tissue fixation block(s). The tissue types can include a cancerous tissue and a non-cancerous tissue, and the first tissue(s) can be identified as the cancerous tissue and the second tissue(s) can be identified as the non-cancerous tissue. The first tissue(s) can be excised.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1:
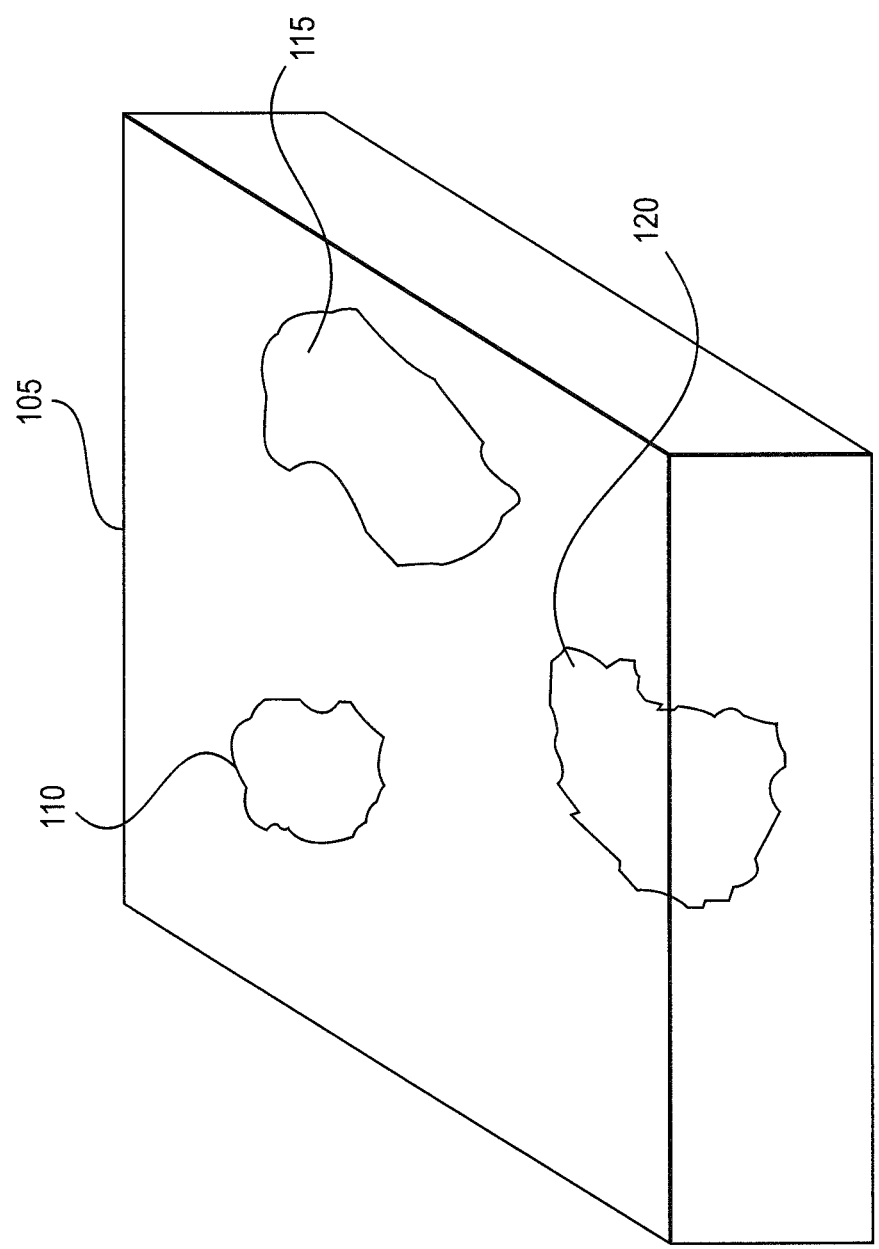
FIG. 1 is a diagram of an exemplary paraffin block having tissue embedded therein which can be used with needles, systems and methods according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

The exemplary system, method and computer-accessible medium can utilize various imaging methods and modalities, including those described in U.S. Pat. No. 8,912,512, the entire disclosure of which is hereby incorporated by reference in its entirety.

The exemplary system, apparatus, method and computer-accessible medium, according to an exemplary embodiment of the present disclosure, can (i) improve biopsy sampling efficacy and efficiency leading to expedited diagnosis and treatment of cancer, (ii) reduce patient risk, and (iii) reduce overall healthcare resource and financial costs. Additionally, the exemplary system, method and computer-accessible medium can facilitate seamless workflow integration, and can benefit from information immediacy and non-destructive specimen handling, such as the interventional radiology suites, operating rooms and high throughput cancer research laboratories.

The exemplary system, apparatus, method and computer-accessible medium, according to another exemplary embodiment of the present disclosure, can include and/or utilize an exemplary instrument that can provide a rapid, tissue-preserving assessment of tumor cellularity in core needle biopsy samples. Neoplastic tissues can undergo structural and biochemical changes that can alter, for example, their spectroscopic profile. The exemplary instrument can be utilized to acquire, analyze and report imaging features (e.g., optical spectra) that can quickly characterize intact biopsy samples (e.g., in less than about one minute), such that feedback regarding biopsy quality and adequacy can be possible during a biopsy procedure. Thus, the exemplary system, method and computer-accessible can facilitate an avoidance of further biopsies at a later point in time as additional biopsies can be taken immediately after the rapid determination of the adequacy of a sample.

Utilizing rapid point-of-acquisition analysis and feedback, the exemplary system, method and computer-accessible medium can establish a new standard for biopsy quality control. The exemplary system, method and computer-accessible medium can be used in both clinical and research domains, and across the spectrum of cancer diagnoses. Higher diagnostic efficiency and efficacy can be achieved, as well as improved patient safety (e.g., minimized tissue sampling procedures). Fewer repeat visits for inadequate specimens can save cost. Additionally, for patients, earlier commencement of effective targeted cancer therapies can be achieved.

The exemplary system, apparatus, method and computer-accessible medium, according to an exemplary embodiment of the present disclosure can utilize spectroscopy or another form of specimen interrogation that (i) does not disrupt the specimen for further processing in Pathology, and/or (ii) facilitate determination of sample adequacy for molecular diagnostic profiling. Thus, DNA, Ribonucleic acid ("RNA"), gene mutations, proteins and/or metabolites can be analyzed and quantified for more specific characterization or diagnosis using the exemplary embodiments of the present disclosure.

Exemplary Analysis of a Paraffin Block

The exemplary system, apparatus, method and computer-accessible medium according to an exemplary embodiment of the present disclosure can be used to analyze tissue (e.g., a combination of cancerous and non-cancerous tissue) contained within one or more tissue fixation blocks (e.g., on or more paraffin blocks), or embedded samples, to determine optimal sites to examine/section for more detailed imaging or histopathologic review. For example, an excised tissue specimen (e.g., tissue 120 shown in FIG. 1) can be embedded in a paraffin block (e.g., block 105 shown in FIG. 1). When the tissue 120 to be analyzed has been embedded in the paraffin block 105, it can be beneficial to separate the cancerous tissue (e.g., tissue 110) from the non-cancerous tissue (e.g., tissue 115) as the non-cancerous tissue 115 can interfere with the test or analysis being performed on the cancerous tissue 110. The cancerous tissue 110 can be separately embedded in paraffin block 105 from the non-cancerous tissue 115 and/or the cancerous tissue 110 and the non-cancerous tissue 115 can be located in the same area of the paraffin block 105 (e.g., tissue 120). In order to separate the cancerous tissue 110 from the non-cancerous tissue 115, the paraffin block 105 can be analyzed (e.g., using spectral analysis), different tissue types can be identified, and the cancerous tissue 110 and the non-cancerous tissue 115 can be separated.

According to an exemplary embodiment of the present disclosure, the paraffin block 105 containing the embedded tissue 120 can be placed in a holder, and then a three-dimensional ("3D") scan of the block can be performed to identify the tissue types (e.g., cancerous or non-cancerous). This exemplary procedure/apparatus/system shall be described further below with reference to FIG. 3.

After the different tissue types can be identified, the non-cancerous tissue 115 can be excised using any suitable method or procedure of physically separating the tissue embedded in a paraffin block. For example, a surgeon or a lab technician can manually cut out the non-cancerous tissue or the cancerous tissue (e.g., using an exemplary drill apparatus). Alternatively or in addition, an exemplary apparatus can be used which can automatically excise the tissue. The cancerous tissue 110, having been separated from the non-cancerous tissue 115, can then be used in various tests, as needed.

The exemplary system, apparatus, method and computer-accessible medium according to an exemplary embodiment of the present disclosure can utilize various agents (e.g., dyes, stains, fluorescent labels, radioactive agents, nuclear magnetic resonance tags) that can label or identify particular biologic components of the sample/tissue (e.g., DNA, proteins, metabolites etc.). This can facilitate a quantification of exemplary biologic components in the sample/tissue.

Information regarding the biologic components of the sample/tissue can be stored in database as a reference for further identifications of biologic components. For example, a library of normal and cancer tissues can serve as the reference for optical spectra analysis using the exemplary system, method and computer-accessible medium. For example, the sample/tissue can be scanned at numerous points, and various spectra can be obtained. These exemplary spectra can be classified as cancerous, non-cancerous, possibly sub-classified by cancer subtype, through an exemplary procedure, and then compared with a library of spectra contained within the database.

According to various exemplary embodiments of the present disclosure, rapid tissue-preserving optical spectroscopy analysis of core biopsy samples can be performed using the exemplary instrument described herein, and can successfully identify tumor-containing samples with a high degree of classification accuracy based on preliminary data. This exemplary instrument can facilitate an improved on-site biopsy assessment. Thus, the exemplary system, apparatus, method and computer-accessible medium, according to an exemplary embodiment of the present disclosure, can facilitate (i) a rapid non-destructive point of acquisition assessment of biopsy adequacy (e.g., tumor quantities) and/or genome/proteome/metabolome quantities in biopsy samples, and/or (ii) an exemplary sample assessment from standard biopsy needles or embedded/preserved samples.

Exemplary Tissue Discrimination in Core Needle Biopsy Specimens

It can be beneficial to utilize feedback to an operator regarding tumor cellularity, as well as genetic content from a sample contained within the biopsy sample. The exemplary system, apparatus, method and computer-accessible medium, according to an exemplary embodiment of the present disclosure, can be used to analyze bone metastases. For example, recognizing the relative frequency of frankly sclerotic or mixed lytic/sclerotic cancer metastases to bone, and the detection of cancer in bone samples can be achieved. Exemplary modalities for rapid assessment of genetic material, proteins or metabolites in a biopsy sample can include, for example, optical, fluorescent, radioactive or other image-able agents such as dyes or vital stains specific for these biologic components. The addition of fluorescence capabilities can improve detection in bone, although alternative approaches, including miniaturized nuclear magnetic resonance detection can be used.

In any sampled tissue type, determining the sufficiency of diagnostic material (e.g., genetic, proteomic, metabolomic) can be important for optimizing and tailoring patient management. It can thus be beneficial to rapidly determine the sufficiency of the DNA sample, for example, immediately after the sample has been taken, and before the sample has been sent to a lab for analysis. This can be because, e.g., it can be possible that there can be insufficient DNA in the sample to perform an analysis of the DNA, but this may not be determined until after the biopsy has been concluded, when a laboratory finally examines the sample. As the exemplary system, apparatus, method and computer-accessible medium, according to an exemplary embodiment of the present disclosure, can facilitate a rapid DNA analysis, a quick, or almost immediate, determination of the sufficiency of the DNA can be made during the biopsy, such that if the amount of DNA can be insufficient, additional samples can be taken at the time of the initial biopsy. Thus, the exemplary system, method and computer-accessible medium, according to an exemplary embodiment of the present disclosure, can ensure that, e.g., only a single biopsy can be needed.

As discussed herein, numerous modalities can be used for rapid sample assessment, including, for example, spectroscopy with the exemplary embodiments according to the present disclosure. Exemplary imaging modalities can utilize either or both inherent tissue properties, or specific imaging agents such as optical, fluorescent, radioactive or other agents including dyes or vital stains known to bind or associate with particular biologic components in a sample.

In order to further enhance the DNA detection specificity, e.g., agents can be introduced to the sample to increase detection specificity, and improve the ability to quantify particular biologic components. For example, according to certain exemplary embodiments, fluorescent dyes can be used to indirectly quantify nuclear DNA content by flow and laser scanning cytometry. Cell-permeant nucleic acid dyes or nuclear counterstains, such as, e.g., Hoechst 33342, can be used can stain fresh core biopsy samples. Excited by UV light and emitting fluorescence when bound to DNA, detection and quantification of these fluorescent types of dyes can be achieved by, for example, integrating a second channel in the instrument for both illumination and detection. In order to avoid cross-talk between the optical and fluorescence channels, and to maintain a short scan time, a synchronized adaptive illumination and detection procedure can be utilized.

The exemplary stains, dyes and labeling agents (e.g., monoclonal antibody-linked labels) can be delivered intravenously or orally to the patient prior to the biopsy, facilitating systemic circulation and specific binding to tissues prior to biopsy. For example, a needle can be dipped into a stain, dye, or labeling agent after removal of the sample, while it is still contained in the needle or extracted onto an imageable cassette/device. Using either in-vivo or ex-vivo labeling, labels can be used that can be specific to DNA, RNA, proteins or other relevant biologic components of the tissue and imaged by the device.

Figure 2:
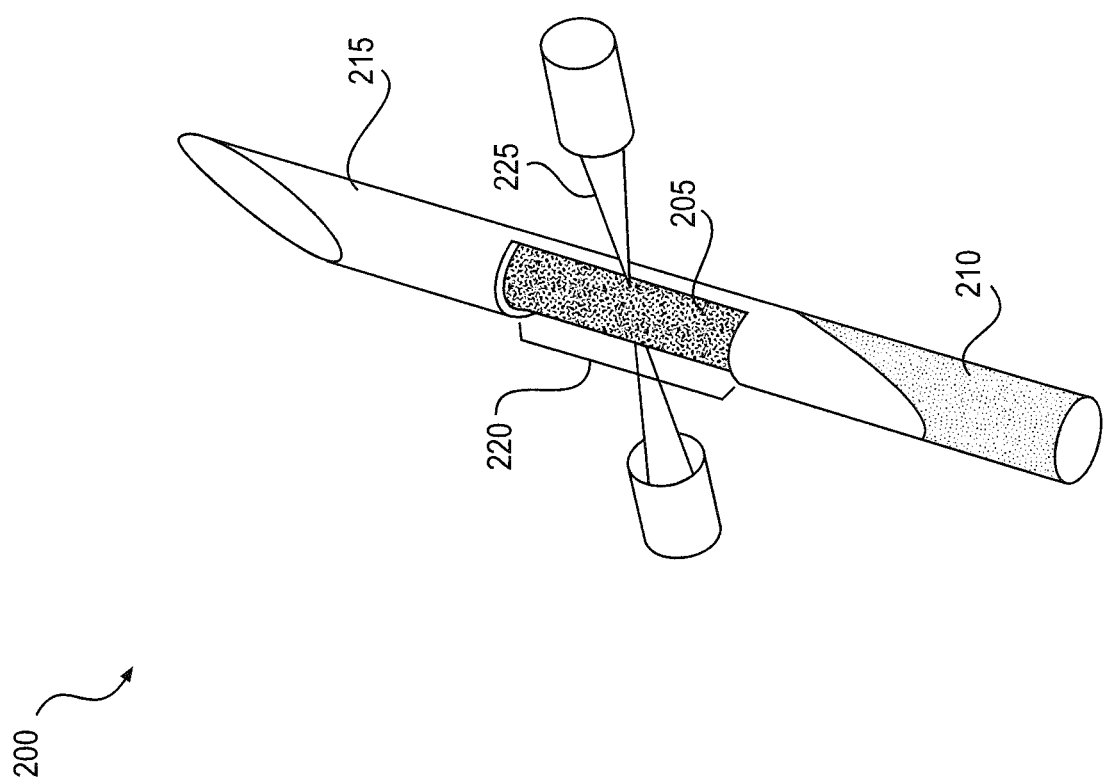
FIG. 2 is a diagram of a biopsy needle containing a biopsy sample (e.g., tissue) according to an exemplary embodiment of the present disclosure.

FIG. 2 illustrates a diagram of a needle unit/arrangement 200 according to an exemplary embodiment of the present disclosure can include a biopsy specimen 205. The exemplary needle unit/arrangement 200 can be a part of, or a component of, an exemplary biopsy collecting device. Such exemplary needle unit/arrangement 200 can be pierced into a patient towards a desired tissue or sample site in order to obtain the biopsy specimen 205 from the patient. The exemplary needle unit/apparatus 200 can include an outer sheath (e.g., cannula 210) and an inner sheath (e.g., stylet 215). The stylet 215 can be configured to extend or retract from the cannula 210. Further, the stylet 215 can have a collection area 220 for collecting the biopsy specimen 205 from the patient.

Upon collecting the biopsy specimen 205 from the patient, the exemplary biopsy collecting device that has the exemplary needle unit/arrangement 200 can be fastened to a needle holder (not shown). For example, the cannula 210 can be fastened to the needle holder, while the stylet 215 can be extended or retracted from the cannula 210. Alternatively or in addition, the stylet 215 can be extended or retracted to position the biopsy specimen 205 across an illumination path 225. The stylet 215 can also be extended or retracted such that the illumination light can scan the biopsy specimen 205 at multiple locations.

Exemplary Spectroscopy System

Figure 3:
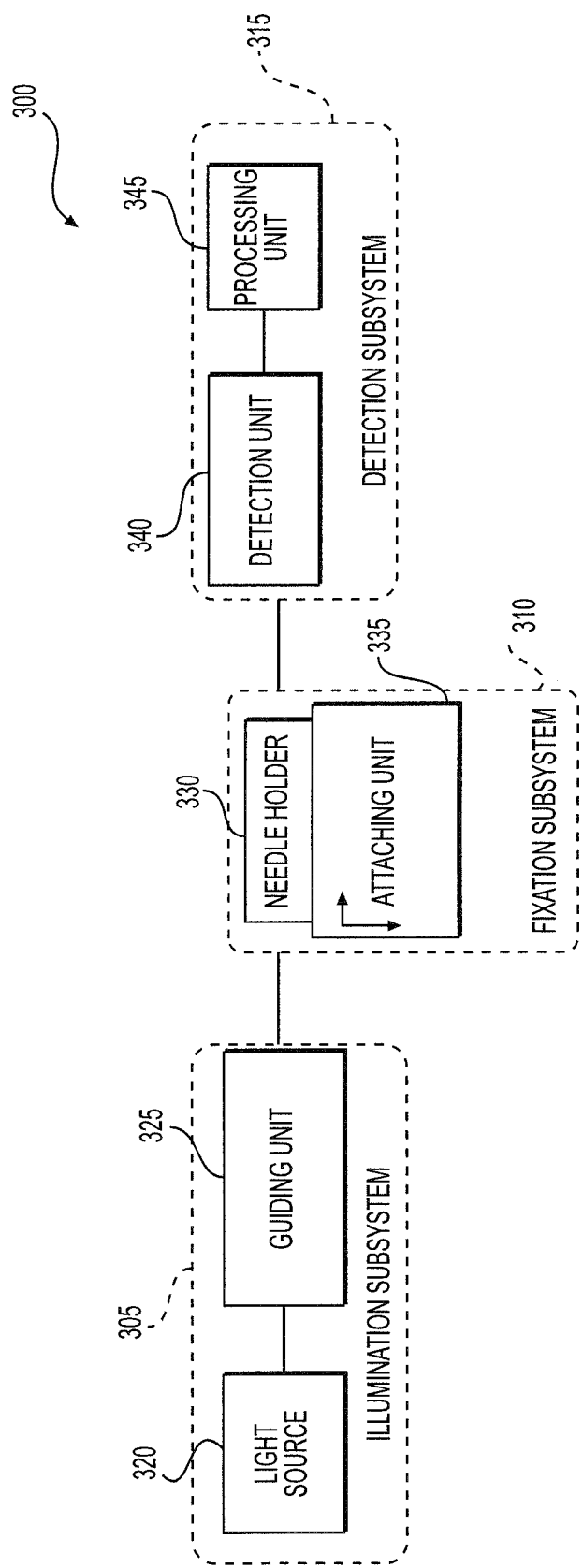
FIG. 3 is a block diagram of a system for analyzing tissue according to an exemplary embodiment of the present disclosure.

FIG. 3 illustrates a block diagram of an exemplary spectroscopy system 300 which can be used for diagnosing tissue (e.g., tissue embedded in paraffin block 100 of FIG. 1, or biopsy sample 205 from FIG. 2) according to an exemplary embodiment of the present disclosure. The exemplary spectroscopy system 300 can be used to determine an amount of diagnostic tissue present in an excised biopsy specimen. In particular, the biopsy specimen can include one or more tissue samples that can be classified into one or more tissue classes, which can facilitate determining a quantity and/or a quality of the diagnostic tissue present in a biopsy specimen. For example, such one or more tissue classes can include a normal tissue class and an abnormal tissue class. The normal tissue class can be referred to as a class of tissue samples having no cancerous tissues (e.g., the non-cancerous tissue 115), such as benign tissue or blood, while the abnormal tissue class can be referred to as a class of tissue samples having cancerous tissues (e.g., the cancerous tissue 110), including a malignant or necrotic tumor, or other diseased tissue such as fibrosis. The exemplary spectroscopy system 300 can be used to characterize the biopsy specimen in a biopsy needle or a biopsy collecting device (e.g., biopsy sample 205 in biopsy needle unit/apparatus 200) immediately after excision. The exemplary biopsy specimen can be referred to as a physical sample of a region in a patient, and can include normal tissue and/or cancerous tissue of a patient.

The exemplary spectroscopy system 300 can include an illumination subsystem/arrangement 305, a fixation subsystem/arrangement 310 and a detection subsystem/arrangement 315. The illumination subsystem/arrangement 305 can be configured to emit an illumination light (or other electromagnetic radiation) towards the biopsy specimen. In one example, the illumination light can have a wavelength in a range from about 200 nm to about 1100 nm although other suitable wavelengths can be used. The exemplary illumination subsystem 305 can include a light source 320, and a guiding unit//arrangement 325 that can be coupled to the light source 320. The light source 320 can include a deuterium tungsten halogen source that can be configured to emit a broadband light towards the biopsy specimen. Further, the guiding unit/arrangement 325 can include optical fibers and/or lenses that can be used for guiding the emitted illumination light towards the biopsy specimen. The guiding unit/arrangement 325 can include a plurality of optical fibers that can be used to deliver the emitted illumination light at multiple locations along the biopsy specimen.

The exemplary fixation subsystem/arrangement 310 can be configured to position the biopsy specimen across the illumination light that can be emitted by the illumination subsystem/arrangement 305. As shown in FIG. 3, the fixation subsystem/arrangement 310 can include a needle holder 330 and an attaching unit/arrangement 335. The needle holder/arrangement 330 can be configured to hold a biopsy collecting device that can include the exemplary biopsy specimen. For example, the exemplary biopsy collecting device can include an activator unit/arrangement and/or a needle unit/arrangement. A portion of the needle unit/arrangement can be pierced into the patient towards a sample/tissue site to obtain the biopsy specimen. Thereafter, the biopsy collecting device can be fastened to the needle holder 330 that can provide an interface between the biopsy collecting device and the detection subsystem 315. In particular, the needle holder 330 can be used for precisely positioning the needle unit/arrangement relative to the illumination light, while scanning the biopsy specimen.

As shown in FIG. 3, the exemplary attaching unit/arrangement 335 can be coupled to the needle holder 310 for positioning the biopsy collecting device at a predetermined position and/or angle in the spectroscopy system 300. For example, the attaching unit 335 can include one or more actuators that can be used for moving the needle holder 330 in a forward or backward direction with respect to an illumination path. Since the needle holder 330 can be provided so as to hold or otherwise maintain the biopsy collecting device, the movement of needle holder 330 can also move the biopsy specimen across the illumination path. This exemplary configuration can facilitate the placement of the biopsy specimen across the illumination light. Thus, the attaching unit 335 can be used for positioning the biopsy collecting device at the predetermined position/angle such that the illumination light can scan the biopsy specimen present in the needle unit.

The exemplary detection subsystem 315 can be coupled to the fixation subsystem 335, and/or can be aligned with the illumination subsystem 305 for determining the diagnostic tissue in the biopsy specimen. The detection modality can be based on a variety of optical detection methods including but not limited to, diffuse optical spectroscopy, fluorescence spectroscopy, optical coherence tomography, Raman spectroscopy or combinations thereof.

The exemplary detection subsystem 315 can include a detecting unit/arrangement 340, and a computer processing unit/arrangement 345. The detecting unit 340 can be used for generating an electrical signal corresponding to a light that can include an attenuated illumination light and/or a re-emitted light from the biopsy specimen. For example, the detecting unit 340 can include one or more optical detectors that can be aligned with the illumination path so as to receive the illumination light emitted by the illumination subsystem 305, and the light re-emitted from the biopsy specimen. The received light may be attenuated by one or more molecules in the biopsy specimen. For example, the molecules in the biopsy specimen can absorb, scatter and/or attenuate the illumination light while passing through the biopsy specimen. This can cause transmission losses at various wavelengths in spectra of the illumination light.

The illumination light with transmission losses can be referred to as the attenuated illumination light. According to some exemplary embodiments of the present disclosure, the received light can include an attenuated illumination light with transmission losses at various wavelengths, which can include information on the absorbance of molecules that include the tissue, the inhomogeneity of the tissue refractive index, and the secondary light re-emitted by molecules due to fluorescence and/or Raman scattering phenomena.

The received and emitted illumination light paths can be provided in more than one direction. For example, the illumination path can be orthogonal or at an oblique angle (e.g., 45 degrees) to the detected light path. Further, the detected light can be converted to a corresponding electrical signal.

The exemplary computer processing unit 345 that can be coupled to the detecting unit 340 can receive one or more electrical signals or data representing the received light. The received electrical signal(s)/data can be processed to determine the diagnostic tissue in the biopsy specimen. For example, the detecting unit 340 can be used, in conjunction with the computer processing unit 345, to analyze the spectrum of the received light c to classify the tissue sample into at least one of the normal tissue class and the abnormal tissue class. Thereafter, the classified tissue sample can be used to determine the quantity and the quality of the diagnostic tissue in the biopsy specimen. After a completion of the analysis, the biopsy specimen can be removed from the biopsy collecting device and transferred to a tissue fixation medium (e.g., formalin) for pathology. By using the exemplary spectroscopy system 300 according to the exemplary embodiment of the present disclosure, the diagnostic tissue within the excised biopsy specimen can be determined without removing the biopsy specimen from the biopsy needle or the biopsy collecting device. In addition, by conducting an analysis directly in the biopsy needle or the biopsy collecting device, it is possible to reduce or otherwise minimize stress on the biopsy specimen/sample and impact on workflow, prior to transferring the biopsy specimen/sample for histopathology or cytopathology.

The exemplary system, apparatus, method and computer-accessible medium, according to an exemplary embodiment of the present disclosure, can facilitate a higher cell nuclei detection specificity, and improved signal-to-noise characteristics around the DNA spectral peak. The translational potential of the exemplary system, apparatus, method and computer-accessible medium, according to an exemplary embodiment of the present disclosure, can extend beyond image-guided needle biopsies to rapid tissue screening and quality control in research laboratories, intraoperative surgical margin analysis and mobile diagnostics.

Figure 4:
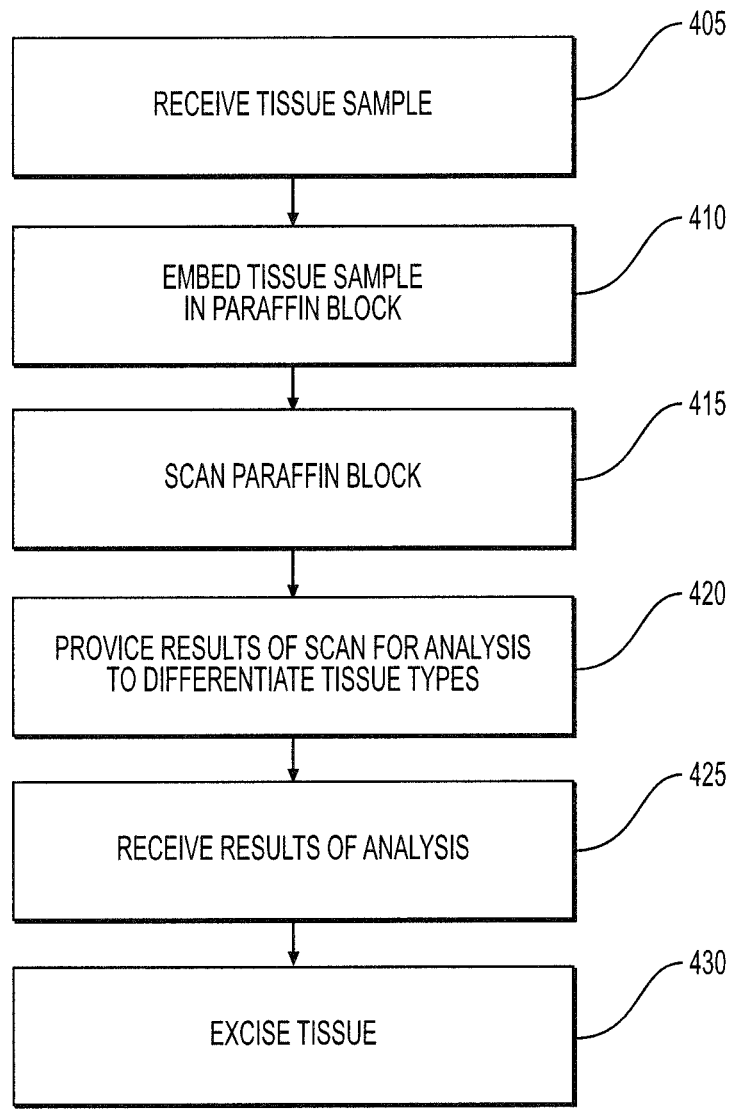
FIG. 4 is a flow diagram of a method for excising the tissue from the paraffin block shown in FIG. 1 according to exemplary embodiments of the present disclosure.

FIG. 4 shows a flow diagram of an exemplary method 400 for excising tissue according to an exemplary embodiment of the present disclosure. For example, at procedure 405, the tissue sample, which can contain cancerous and/or non-cancerous tissue(s) 110, 115, can be received. At procedure 405, the tissue can be embedded in a block (e.g., the paraffin block 105), and the block 105 can be scanned at procedure 415. At procedure 420, the results of the scan from procedure 415 can be provided to a system that can analyze the block 105 to determine the tissue type of the tissue sample in the block 105. At procedure 425, the results of the analysis can be received, and the tissue (e.g., either the cancerous tissue and/or non-cancerous tissue(s) 110, 115) can be excised from the paraffin block 105 at procedure 430.

Figure 5:
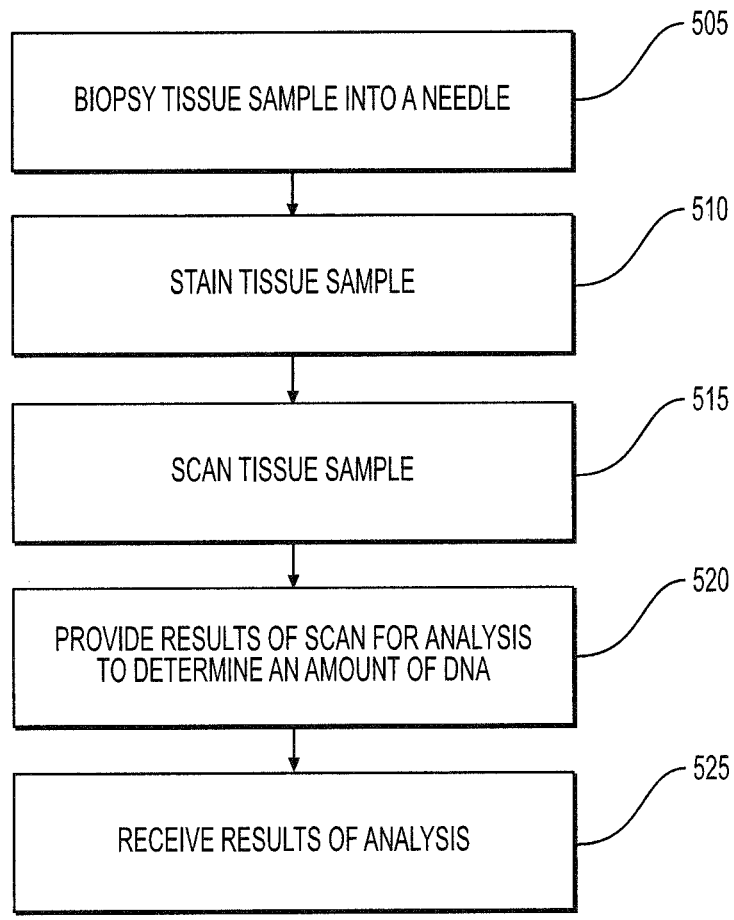
FIG. 5 is a flow diagram of a method for determining a DNA quantity of the sample in the biopsy needle shown in FIG. 2 according to exemplary embodiments of the present disclosure.

FIG. 5 shows a flow diagram of a method 500 for determining a DNA quantity of the sample according to an exemplary embodiment of the present disclosure. For example, at procedure 505, a biopsy needle (e.g., the needle unit 200) can be used to biopsy a tissue sample from a patient. The tissue sample can be stained at procedure 510, and then scanned at procedure 515. At procedure 520, the exemplary results of the scan can be provided to a system for determining an amount of DNA contained within the tissue sample, and the results of the amount of DNA in the tissue sample can be received at procedure 525.

Figure 6:
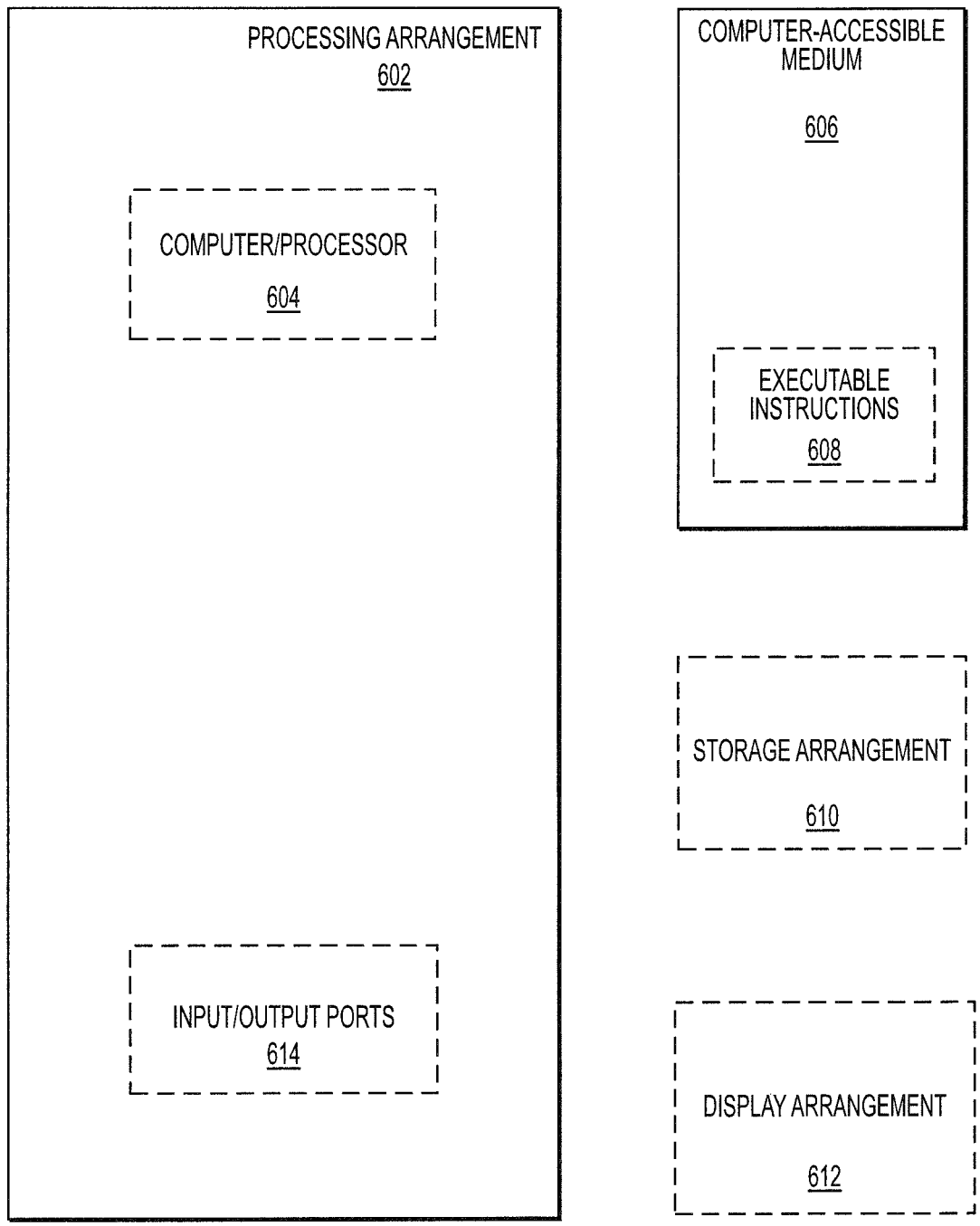
FIG. 6 is a block diagram of an exemplary system in accordance with certain exemplary embodiments of the present disclosure.

FIG. 6 illustrates a block diagram of an exemplary embodiment of a system according to the present disclosure. For example, exemplary procedures in accordance with the present disclosure described herein can be performed by a processing arrangement and/or a computing arrangement 602. Such processing/computing arrangement 602 can be, for example entirely or a part of, or include, but not limited to, a computer/processor 604 that can include, for example one or more microprocessors, and use instructions stored on a computer-accessible medium (e.g., RAM, ROM, hard drive, or other storage device).

As shown in FIG. 6, for example a computer-accessible medium 606 (e.g., as described herein above, a storage device such as a hard disk, floppy disk, memory stick, CD-ROM, RAM, ROM, etc., or a collection thereof) can be provided (e.g., in communication with the processing arrangement 602). The computer-accessible medium 606 can contain executable instructions 608 thereon. In addition or alternatively, a storage arrangement 610 can be provided separately from the computer-accessible medium 606, which can provide the instructions to the processing arrangement 602 so as to configure the processing arrangement to execute certain exemplary procedures, processes and methods, as described herein above, for example.

Further, the exemplary processing arrangement 602 can be provided with or include an input/output arrangement 614, which can include, for example a wired network, a wireless network, the interne, an intranet, a data collection probe, a sensor, etc. As shown in FIG. 6, the exemplary processing arrangement 602 can be in communication with an exemplary display arrangement 612, which, according to certain exemplary embodiments of the present disclosure, can be a touch-screen configured for inputting information to the processing arrangement in addition to outputting information from the processing arrangement, for example. Further, the exemplary display 612 and/or a storage arrangement 610 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. A non-transitory computer-accessible medium having stored thereon computer-executable instructions, wherein, when a computer arrangement executes the instructions, the computer arrangement is configured to perform procedures comprising:
    generating information related to at least one tissue fixation block having both a diseased tissue and a normal tissue embedded in the at least one tissue fixation block;
    identifying, based on the generated information, both the diseased tissue and the normal tissue which are different from one another and both provided in the at least one tissue fixation block; and
    excising, based on the identification, at least one of the identified diseased tissue or the identified normal tissue from the at least one tissue fixation block.

2. The computer-accessible medium of claim 1, wherein the at least one tissue fixation block is a paraffin block.

3. The computer-accessible medium of claim 1, wherein the information is a result of a three-dimensional scan of the at least one tissue fixation block.

4. The computer-accessible medium of claim 3, wherein the computer arrangement is further configured to perform the three-dimensional scan using a computed tomography arrangement.

5. The computer-accessible medium of claim 1, wherein the computer arrangement is further configured to perform procedures comprising embedding the diseased tissue and the normal tissue in the at least one tissue fixation block.

6. The computer-accessible medium of claim 1, wherein the computer arrangement performs the identification for both the diseased tissue and the normal tissue which are both embedded in the same block of the at least one tissue fixation block.

7. The computer-accessible medium of claim 1, wherein, prior to the generation of the information, selecting both the diseased tissue and the normal tissue to be embedded in the at least one tissue fixation block.

8. A system comprising:
    at least one tissue fixation block having both a diseased tissue and a normal tissue embedded therein; and
    a computer hardware arrangement configured to:
        generate information related to the at least one tissue fixation block;
        identify, based on the generated information, both the diseased tissue and the normal tissue which are different from one another and both provided in the at least one tissue fixation block; and
        excise, based on the identification, at least one of the identified diseased tissue or the identified normal tissue from the at least one tissue fixation block.

9. The system of claim 8, wherein the computer hardware arrangement is further configured to embed the diseased tissue and the normal tissue in the at least one tissue fixation block.

10. The system of claim 8, wherein the tissue fixation block is a paraffin block.

11. The system of claim 8, wherein the information is a result of a three-dimensional scan of the at least one tissue fixation block.

12. The system of claim 8, wherein the computer arrangement performs the identification for both the diseased tissue and the normal tissue which are both embedded in the same block of the at least one tissue fixation block.

13. The system of claim 8, wherein, prior to the generation of the information, selecting both the diseased tissue and the normal tissue to be embedded in the at least one tissue fixation block.

14. A method comprising:
    embedding both a diseased tissue and a normal tissue in at least one tissue fixation block;
    generating information related to the at least one tissue fixation block by scanning the at least one tissue fixation block;
    using a computer hardware arrangement and based on the generated information, identifying both the diseased tissue and the normal tissue which are different from one another and both embedded in the at least one tissue fixation block; and
    excising, based on the identification, at least one of the identified diseased tissue or the identified normal tissue from the at least one tissue fixation block.

15. The method of claim 14, further comprising labelling at least one of the diseased tissue or the normal tissue using at least one of (i) a dye, (ii) a stain, (iii) a fluorescent label, (iv) a radioactive agent, or (v) a nuclear magnetic resonance tag.

16. The method of claim 14, wherein the tissue fixation block is a paraffin block.

17. The method of claim 14, wherein the information is a result of a three-dimensional scan of the at least one tissue fixation block.

18. The method of claim 14, wherein the computer arrangement is further configured to perform the three-dimensional scan using a computed tomography arrangement.

19. The method of claim 14, wherein the identification is performed for both the diseased tissue and the normal tissue which are both embedded in the same block of the at least one tissue fixation block.

20. The method of claim 14, further comprising, prior to the embedding, selecting both the diseased tissue and the normal tissue to be embedded in the at least one tissue fixation block.

\* \* \* \* \*